(12) United States Patent
Azizgolshani et al.

(10) Patent No.: US 11,760,967 B2
(45) Date of Patent: Sep. 19, 2023

(54) SYSTEMS AND METHODS FOR SEEDING CELL CULTURES IN A MICROFLUIDIC DEVICE

(71) Applicant: Charles Stark Draper Laboratory, Inc., Cambridge, MA (US)

(72) Inventors: Hesham Azizgolshani, Belmont, MA (US); Brian Cain, Cambridge, MA (US); Joseph Charest, Cambridge, MA (US); Jonathan Robert Coppeta, Windham, NH (US); Brett Isenberg, Newton, MA (US); Timothy Petrie, Braintree, MA (US)

(73) Assignee: Charles Stark Draper Laboratory, Inc., Cambridge, MA (US)

( * ) Notice: Subject to any disclaimer, the term of this patent is extended or adjusted under 35 U.S.C. 154(b) by 261 days.

(21) Appl. No.: 17/013,454

(22) Filed: Sep. 4, 2020

(65) Prior Publication Data

US 2021/0071125 A1    Mar. 11, 2021

Related U.S. Application Data

(60) Provisional application No. 62/896,121, filed on Sep. 5, 2019.

(51) Int. Cl.
*C12M 3/06*    (2006.01)
*C12M 1/12*    (2006.01)
(Continued)

(52) U.S. Cl.
CPC ............ *C12M 23/16* (2013.01); *C12M 25/02* (2013.01); *C12M 25/14* (2013.01); *C12M 33/00* (2013.01);
(Continued)

(58) Field of Classification Search
CPC ...... C12M 23/16; C12M 25/02; C12M 25/14; C12N 1/00; B01L 3/50255; B01L 3/502753; B01L 2300/0681
See application file for complete search history.

(56) References Cited

U.S. PATENT DOCUMENTS 8,435,738 B2 *  5/2013  Holmes .................. G01N 21/07
                                                    435/7.1
2004/0069717 A1   4/2004  Laurell et al.
(Continued)

FOREIGN PATENT DOCUMENTS

WO    WO-2016/168091 A1    10/2016
WO    WO-2018/098169 A1     5/2018

OTHER PUBLICATIONS

International Preliminary Report on Patentability on PCT Appln. PCT/US2020/049562 dated Mar. 17, 2022 (7 pages).
(Continued)

*Primary Examiner* — Sean C. Barron
(74) *Attorney, Agent, or Firm* — Foley & Lardner LLP

(57) ABSTRACT

This disclosure provides systems and methods for seeding cell cultures in a microfluidic device. The systems and methods of this disclosure can enable flow of a cell solution from one side of a scaffold, such as a porous substrate or membrane, to the other side of the scaffold. Flow of the liquid can pass through the scaffold while the cells themselves do not, resulting in the cells driven to the surface of the scaffold for consequent attachment. A microfluidic device can include a microfluidic feature structured to create a seal between a cell seeding tool and an inlet to a microchannel of the microfluidic device. This can enable a pressure-driven flow to push fluid down the channel and through pores of the membrane. In contrast, traditional gravity fed (Continued)

seeding of cells may not create enough pressure to drive fluid through the pores of the scaffold.

17 Claims, 9 Drawing Sheets

(51) Int. Cl.
  *C12M 1/26*     (2006.01)
  *C12N 1/00*     (2006.01)
  *B01L 3/00*     (2006.01)

(52) U.S. Cl.
  CPC ..... *B01L 3/50255* (2013.01); *B01L 3/502753* (2013.01); *B01L 2300/0681* (2013.01); *C12N 1/00* (2013.01)

(56) References Cited

U.S. PATENT DOCUMENTS

| | | | |
|---|---|---|---|
| 2012/0244043 A1* | 9/2012 | Leblanc | B01L 3/502715 422/504 |
| 2014/0065660 A1 | 3/2014 | Kim et al. | |
| 2018/0221874 A1* | 8/2018 | Parker | G01N 33/5061 |

OTHER PUBLICATIONS

International Search Report and Written Opinion on PCT Appln. PCTUS2020/049562 dated Nov. 24, 2020 (126 pages).

* cited by examiner

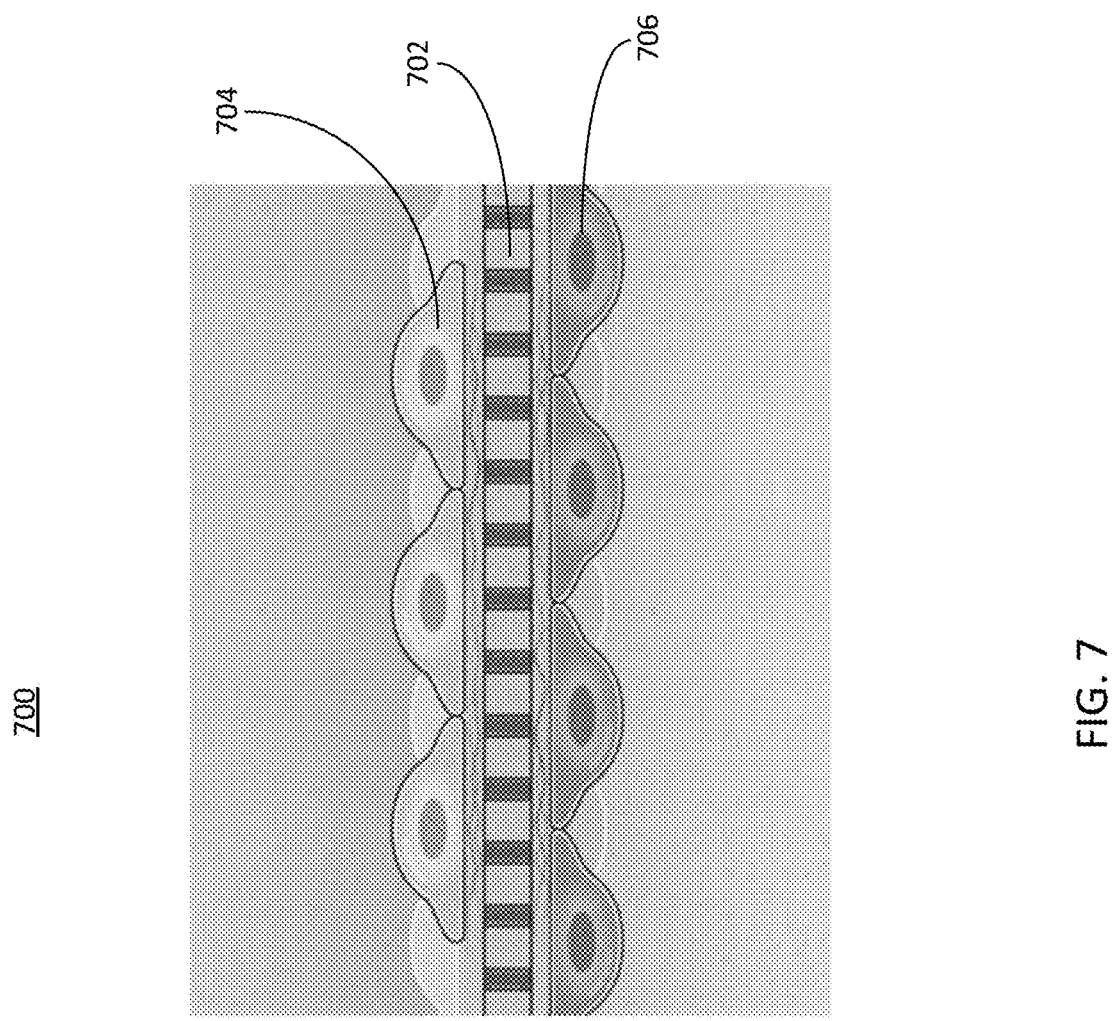

SYSTEMS AND METHODS FOR SEEDING CELL CULTURES IN A MICROFLUIDIC DEVICE

CROSS REFERENCE TO RELATED APPLICATIONS

The present application claims priority under 35 U.S.C. § 119(e) to U.S. Provisional Patent Application No. 62/896,121, titled "SYSTEMS AND METHODS FOR SEEDING CELL CULTURES IN A MICROFLUIDIC DEVICE," filed Sep. 5, 2019, which is incorporated herein in its entirety by reference.

BACKGROUND

Microfluidic devices can include features such as channels, chambers, and wells. It can be challenging to utilize such devices for culturing cells, because it is challenging to introduce cell cultures to scaffolding or other cell attachment features.

SUMMARY

The present disclosure describes systems and methods for seeding cell cultures in a microfluidic device. The microfluidic device can include features such as wells, chambers, or channels, at least some of which can be used for culturing a respective group of cells. In some implementations, the microfluidic device can include 96 wells arrayed in a rectangular grid pattern. Using conventional microfluidic devices and cell seeding techniques can present a variety of technical challenges. For example, cell seeding may be limited by gravity causing cells to settle down onto a cell adhesive surface, which can also be referred to as a scaffold. As a result, it can be difficult to seed cells on both sides of a scaffold. In addition, it may be difficult to seed cells in a limited area that is suitable for active analysis of the cells. For example, because cell seeding can rely on gravity to pull the cells downward, precise control over the final position of all cells on the scaffold can be difficult to achieve. Thus, some cells may be seeded in positions that are outside the area of interest where culture conditions are well controlled and analysis of those cells can take place. Finally, conventional cell seeding techniques are traditionally limited to using a membrane for the cell scaffold or cell adhesive surface.

The systems and methods of this disclosure include microfluidic devices as well as cell seeding techniques that can overcome the drawbacks described above. In some implementations, the systems and methods of this disclosure can enable flow of a cell solution from one side of a scaffold, such as a porous substrate, to the other side of the scaffold. Flow of the liquid can pass through the scaffold while the cells themselves do not, resulting in the cells driven to the surface of the scaffold for consequent attachment. In typical systems, the pressure to drive liquid through a porous substrate can be too low and the solution may therefore only move across the surface of the scaffold and not deposit cells onto the surface of the scaffold. To address this challenge, a microfluidic device can be designed to include a microfluidic feature structured to create tight fit (e.g., forming a seal) between a cell seeding tool (e.g., a pipettor or other liquid handling tool) and an inlet to a microchannel of the microfluidic device. This can enable a pressure-driven flow to push fluid down the channel and through pores of the membrane. In contrast, traditional gravity fed seeding of cells may not create enough pressure to drive fluid through the pores of a scaffold, because the pores may have significant resistance to flow due to their diameters, which can range from 0.4 μm to 8 μm, for example.

At least one aspect of the present disclosure is generally directed to a microfluidic device. The microfluidic device can include a first channel having a first inlet port and a first outlet port. The first channel can be configured to receive a fluid sample comprising cells. The microfluidic device can include a second channel coupled to the first channel via an overlapping region. The second channel can have a second inlet port and a second outlet port. The microfluidic device can include an overlapping region between the first channel and the second channel. The overlapping portion can be configured to trap the cells in the fluid sample as the fluid sample flows through the first channel.

In some implementations, the overlapping region can form a bottom portion of the first channel and forms a top portion of the second channel. In some implementations, at least one of the first inlet port, first outlet port, second inlet port, or second outlet port can be coupled to a well of a well plate. In some implementations, the overlapping region can include a semipermeable membrane configured to allow the fluid sample to flow from the first channel to the second channel while trapping the cells in the fluid sample on a surface of the semipermeable membrane in the first channel.

In some implementations, the overlapping region can be further configured to trap cells in a second fluid sample on a second surface of the semipermeable membrane in the second channel while allowing a second fluid sample to flow from the second channel to the first channel. In some implementations, the overlapping region can include at least one of a membrane, a filter, a mesh, or a scaffold. In some implementations, one or more portions of the overlapping region can be chemically treated by at least one of a coating, an energetic plasma treatment, affixing the one or more surfaces with a self-assembled monolayer, or surface depositing.

In some implementations, an opening of at least one of the first inlet port, the second inlet port, the first outlet port, or the second outlet port can be defined by a first width and can include a tapered portion defining a second width, and is configured to receive a portion of a cell seeding tool. In some implementations, the tapered portion can include at least one of a squared tapering or a rounded tapering. In some implementations, the tapered portion can include one or more flanges arranged concentrically with the taper that mechanically flex to accommodate the cell seeding tool. In some implementations, the opening of at least one of the first inlet port, the second inlet port, the first outlet port, or the second outlet port comprises at least one of a gasket or a spacer configured to create a seal with the portion of the cell seeding tool. In some implementations, an opening of at least one of the first inlet port, the second inlet port, the first outlet port, or the second outlet port can include at least one of one or more fins, a chamfer, a countersink, or an extension into a well of a well plate.

At least one other aspect of the present disclosure is generally directed to a system. The system can include a semipermeable membrane having a first surface and a second surface opposite the first surface. Each of the first surface and the second surface can be configured to trap cells in a fluid sample. The system can include a first channel coupled to the semipermeable membrane. The first channel can have a first portion defined by the first surface of the semipermeable membrane. The system can include a second channel coupled to the semipermeable membrane. The second channel can have a second portion defined by the second surface of the semipermeable membrane. The semipermeable membrane can be configured to allow the fluid sample to flow between the first channel and the second channel.

In some implementations, the semipermeable membrane can include at least one of a membrane, a filter, a mesh, or a scaffold. In some implementations, the semipermeable membrane can be further configured to trap, on the first surface, first cells of a first fluid sample flowing from the first channel to the second channel. In some implementations, the semipermeable membrane can be further configured to trap, on the second surface, second sells of a second fluid sample flowing from the second channel to the first channel. In some implementations, a portion of the semipermeable membrane can be configured to limit cell attachment. In some implementations, at least a portion of the semipermeable membrane can be chemically treated by at least one of a coating, an energetic plasma treatment, affixing the one or more surfaces with a self-assembled monolayer, or surface depositing.

At least one other aspect of the present disclosure is generally directed to a method. The method can include receiving, by a first channel of a microfluidic device, a cell seeding tool configured to deliver a fluid sample comprising cells. The method can include receiving, by the first channel of the microfluidic device, the fluid sample via the cell seeding tool. The fluid sample can have a fluid pressure generated by the cell seeding tool. The method can include guiding, by the microfluidic device, a portion of the fluid sample through a semipermeable membrane of the microfluidic device using the first channel and the fluid pressure. The method can include trapping, by a first surface of the semipermeable membrane of the microfluidic device, the cells of the fluid sample within the first channel. The method can include guiding, by the microfluidic device, the portion of the fluid sample less the trapped cells to a second channel coupled to the semipermeable membrane.

In some implementations, the method can include receiving, by the second channel of the microfluidic device, a second cell seeding tool configured to deliver a second fluid sample comprising second cells. In some implementations, the method can include receiving, by the second channel of the microfluidic device, the second fluid sample via the second cell seeding tool. In some implementations, the method can include trapping, by a second surface of the semipermeable membrane of the microfluidic device, the second cells of the fluid sample within the second channel. In some implementations, the second surface of the semipermeable membrane can be opposite the first surface of the semipermeable membrane. In some implementations, receiving the cell seeding tool can include creating, by the first channel of the microfluidic device, a seal with the cell seeding tool to generate fluid pressure used to guide the portion of the fluid sample through the semipermeable membrane of the microfluidic device.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. The foregoing and other objects, aspects, features, and advantages of the disclosure will become more apparent and better understood by referring to the following description taken in conjunction with the accompanying drawings, in which:

FIG. 7 illustrates a cross-sectional view of an example cell scaffold, in accordance with an illustrative embodiment.

DETAILED DESCRIPTION

Figure 1:
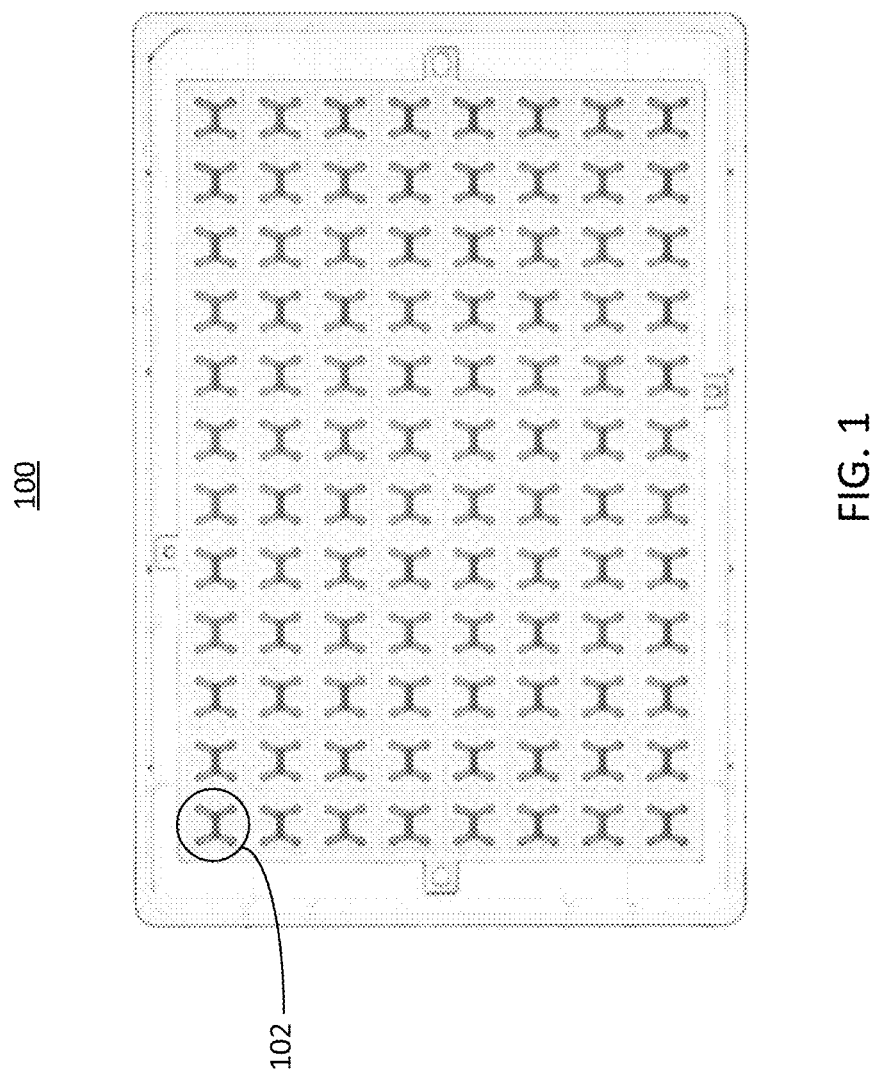
FIG. 1 illustrates a top view of an example well plate, in accordance with an illustrative embodiment.

The various concepts introduced above and discussed in greater detail below may be implemented in any of numerous ways, as the described concepts are not limited to any particular manner of implementation. Examples of specific implementations and applications are provided primarily for illustrative purposes.

Using conventional microfluidic devices and cell seeding techniques can present a variety of technical challenges. Cell seeding may be limited by gravity, which causes cells to settle down onto a cell adhesive surface, which can also be referred to as a scaffold. As a result, it can be difficult to seed cells on both sides of a scaffold. When using other cell seeding techniques, it is difficult to seed cells in a limited area that is suitable for active analysis of the cells. Because cell seeding can rely on gravity to pull the cells downward, precise control over the final position, pattern, or placement of all cells on the scaffold can be difficult to achieve. Thus, some cells may be seeded in positions that are outside the area of interest where culture conditions are well controlled and analysis of those cells can take place. Finally, conventional cell seeding techniques are traditionally limited to using a membrane for the cell scaffold or cell adhesive surface.

To address at least the issues outlined above, the systems and methods described herein can provide one or more microfluidic devices for seeding cell cultures. The microfluidic device can include features such as wells, chambers, or channels, at least some of which can be used for culturing a respective group of cells. In some implementations, one or more microfluidic devices can be coupled to, or form a part of, a well plate. The number of microfluidic devices that are coupled to or form a part of the well plate can be a based on the number of wells in the well plate. An example well plate can include up to 96 wells. The wells on a well plate can be arranged in a number of different ways. One such arrangement can include a rectangular grid pattern. Other arrangements can include a circulator arrangement, a honeycomb arrangement, or any other type of arrangement. It should be understood that although some of the microfluidic channels depicted herein can couple to or form a part of a well plate having wells in a rectangular arrangement, other arrangements are possible. The size, shape, and particular arrangement of the microfluidic channels may be changed to accommodate well plate arrangements other than rectangular arrangements.

This disclosure describes microfluidic devices as well as cell seeding techniques that can overcome the drawbacks described above. The systems and methods of this disclosure can enable flow of a cell solution from one side of a scaffold (e.g., or any other type of permeable membrane or barrier through which fluid may flow, etc.), such as a porous substrate or other medium, to the other side of the scaffold. Flow of the liquid can pass through the scaffold while the cells themselves do not, resulting in the cells driven to the surface of the scaffold for consequent attachment. The pressure driving liquid through a porous substrate or other medium can be such that and the solution passes through the barrier while depositing cells on surface of the barrier. Because the fluid flow can be driven by external pressure and not simply by gravity, the techniques described herein can cause cells that would otherwise be difficult to seed to adhere to a membrane surface. Further, deposition of cells on a surface that would otherwise oppose the force of gravity is possible, causing more than one surface of a substrate to be precisely seeded with cells.

FIG. 1 illustrates a top view of an example well plate 100. As shown in the figure, the wells of the well plate 100 are coupled to a series of microfluidic devices 102 (sometimes referred to as cell culture unit(s) 102). In some implementations, the microfluidic devices 102 can comprise one or more channels with inlets and outlets that are coupled to the wells of the well plate 100. The microfluidic device 102 can include two or more channels that share an overlapping region. The implementation illustrated in FIG. 1 includes microfluidic devices 102 having two overlapping channels, where each overlapping channel has an inlet port and an outlet port. In some implementations, the inlet port and the outlet ports of the microfluidic devices can be bidirectional (e.g., serve as either an inlet port or an outlet port, etc.). The ports of the microfluidic device can be formed as part of the wells of the well plate 100, or may be coupled to the wells of the well plate through adhesion, mechanical coupling, or other coupling means.

The microfluidic devices 102 can be arranged in a pattern across to accommodate the wells of the well plate, or any other openings of substrates in implementations where a well plate is not present. The arrangement of the channels of each microfluidic device 102 can change to accommodate the shape of the wells or openings of the well plate 100, or any other substrate to which the microfluidic device is coupled. In FIG. 1, the well plate 100 is depicted as including 96 microfluidic devices 102 arranged in a 12 by 8 grid, however it should be understood that other arrangements, which may include more or fewer microfluidic devices 102, are also possible. In some implementations, the well plate 100 can have more or fewer wells or openings, which may be arranged differently than what is depicted in FIG. 1. Further, in some implementations, each channel of the microfluidic device 102 may have more than or fewer than two openings. For example, in some implementations, a microfluidic device 102 may have channels each having one opening, where fluid flow is facilitated through each channel via the overlapping region of the channels. Each microfluidic device 102 can serve as an area for one or more cell cultures to be introduced, for example by cell seeding techniques. In some implementations, other substances, such as therapeutic substances, can be introduced into the microfluidic devices 102, and their interactions with the cell cultures can be observed or measured. The structure of the microfluidic device 102 is described in further detail below in conjunction with FIG. 2.

Figure 2:
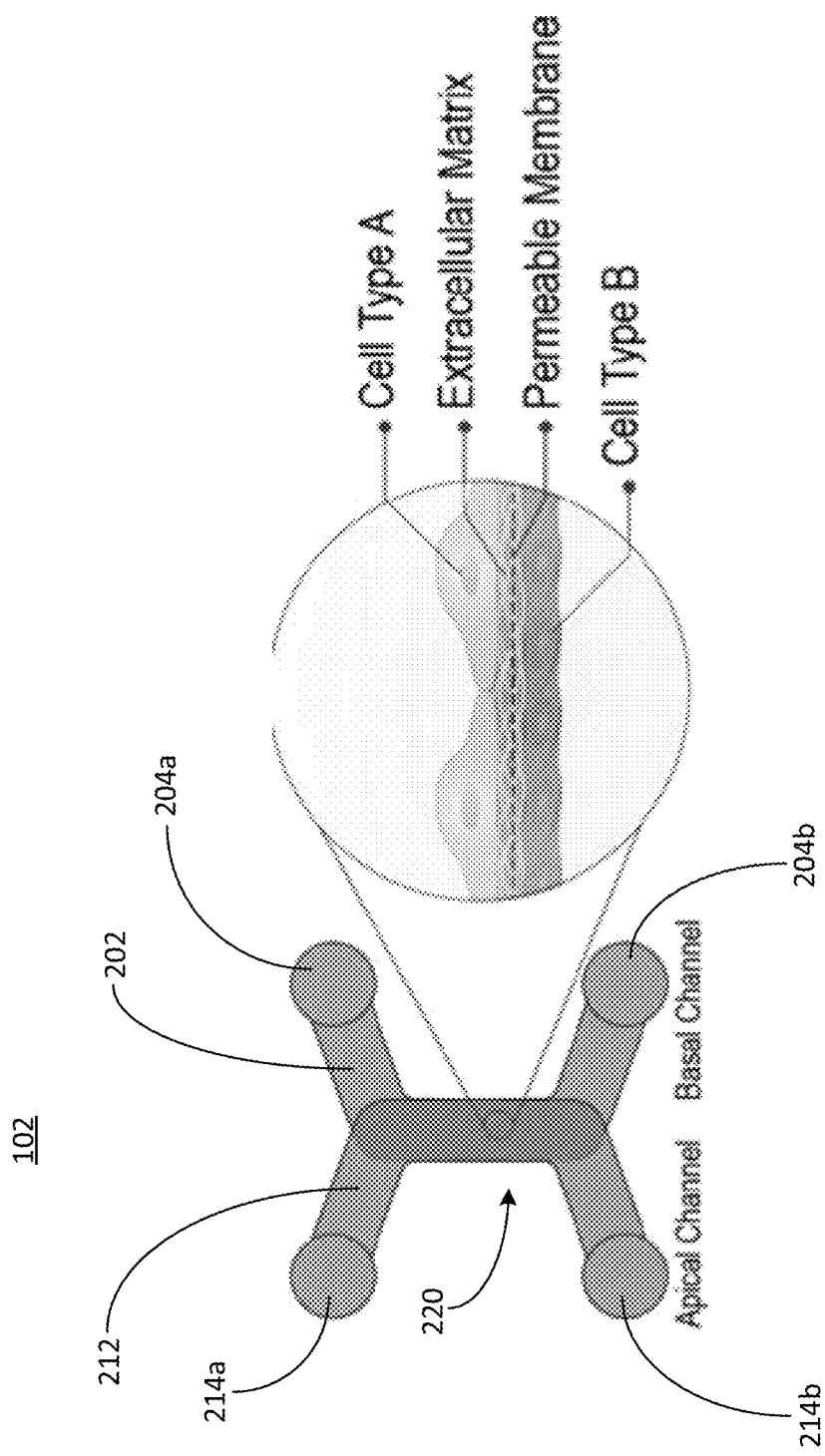
FIG. 2 illustrates a top view of an example microfluidic channels of an example well plate, in accordance with an illustrative embodiment.

Referring now to FIG. 2, depicted is a top view of an example microfluidic device. The microfluidic device 102 can have at least one channel having one or more openings, which can be a part of or coupled to the well plate 100 described herein above in conjunction with FIG. 1. The channels of the microfluidic device may be formed from any suitable material to facilitate the flow of fluid, for example a plastic substrate, a metal substrate, a polymer substrate, a ceramic material, a composite material substrate, or any other type of material suitable for forming microfluidic channels. In some implementations, the microfluidic device 102 can be formed as a part of a well plate, such as the well plate 100 described herein above in conjunction with FIG. 1. The microfluidic device 102 or the components thereof may be formed by various processes, including wet etching, reactive ion etching, conventional machining, photolithography, soft lithography, injection molding, laser ablation, in situ construction, plasma etching, or any combination thereof.

The microfluidic device 102 can include a basal channel 202. The basal channel can include two ports 204a and 204b (generally referred to as ports 204), each of which can serve as either an inlet port, an outlet port, or both (e.g., each port may serve as either an inlet port or an outlet port, etc.). The ports 204 of the basal channel 202 can be openings in the channel 202 that are configured to receive a fluid, such as a fluid containing cells for a cell seeding or culturing process. Although the basal channel 202 is depicted as having two ports, it should be understood that the ports 204 can be any number of ports (e.g., one port 204, two ports 204, three ports 204, etc.). The ports 204 can be coupled to one or more wells of the well plate 100, or can be formed as a part of one or more wells of the well plate 100. In some implementations, the ports 204 are openings to the basal channel 202, and are not coupled to a well plate or formed as a part of a well plate. Thus, the microfluidic device 102 can exist in a number of different configurations, such as part of a well plate, or coupled to a different type of device for cell culturing. Particular configurations of the ports 204 of the basal channel 202, the ports 214 of the apical channel 212, or any other ports or openings described herein, are described herein below in conjunction with FIGS. 5, 6A, and 6B.

The microfluidic device 102 can include an apical channel 212. The apical channel 212 can include two ports 214a and 214b (generally referred to as ports 214). The ports 214 of the apical channel 212 can be openings in the channel 202 that are configured to receive a fluid, such as a fluid containing cells for a cell seeding or culturing process. Although the apical channel 212 is depicted as having two ports, it should be understood that the ports 214 can be any number of ports (e.g., one port 204, two ports 214, three ports 214, etc.). The ports 214 can be coupled to one or more wells of the well plate 100, or can be formed as a part of one or more wells of the well plate 100. In some implementations, the ports 214 are openings to the apical channel 212, and are not coupled to a well plate or formed as a part of a well plate. Thus, the microfluidic device 102 can exist in a number of different configurations, such as part of a well plate, or coupled to a different type of device for cell culturing. Configurations of the ports 204 of the basal channel 202, the ports 214 of the apical channel 212, or any other ports or openings described herein, are described herein below in conjunction with FIGS. 5, 6A, and 6B.

The microfluidic device 102 can include an overlapping portion 220 (sometimes referred to as an overlapping region 220) in which the basal channel 202 and the apical channel 212 overlap one another. By way of non-limiting example, the basal channel 202 can be disposed beneath the apical channel 212, and the overlapping region 220 can form a top wall of the basal channel 202, and a bottom wall of the apical channel 212. Thus, the overlapping portion 220 can form a portion of each of the apical channel 212 and the basal channel 202. In some implementations, the apical channel 212 and the basal channel 202 can be disposed differently with respect to one another, but share an overlapping region that forms a portion of either channel. In some implementations, the overlapping portion 220 can be formed as part of the microfluidic device, or may be disposed among one or more layers of the microfluidic device. In some implementations, the overlapping portion 220 can be fixed in place by mechanical force, an adhesive, or formed as part of at least one of the basal channel 202 or the apical channel 212.

The overlapping region 220 can be configured to trap and grow cell cultures, for example cell cultures or cells within a fluid sample that passes through at least one of the apical channel 212 or the basal channel 202. The overlapping portion 220 can be porous, or otherwise semipermeable, thus facilitating flow of one or components of a fluid between the basal channel 202 and the apical channel 212, or vice versa. The overlapping portion 220 can be made of materials other than the materials that define the basal channel 202 or the apical channel 212. For example, the overlapping portion can be or include any of a membrane (e.g., a semipermeable membrane, etc.), a filter, a mesh, or any other substance that allows some or all of a fluid to pass through the overlapping portion 220. Thus, the overlapping portion 220 can facilitate the flow of a fluid sample between the basal channel 202 and the apical channel 212, while trapping cells in the fluid sample on the respective portion of the membrane within one of the apical channel 212 or the basal channel 202. For example, if a fluid sample containing cells passes through the barrier from the basal channel 202 into the apical channel 212, the overlapping portion 220 can trap the cells in the fluid sample on the surface of the overlapping portion 220 within the basal channel 202. Likewise, if a fluid sample containing cells passes through the barrier from the apical channel 212 into the basal channel 202, the overlapping portion 220 can trap the cells in the fluid sample on the surface of the overlapping portion 220 within the apical channel 212.

The overlapping portion 220 can include a cell scaffold such as a permeable membrane, as shown in the enlarged view on the right of FIG. 2. The scaffold can, at least in part, separate the basal channel 202 from the apical channel 212 in the overlapping portion 220. In some implementations, a cell culture (e.g., a fluid sample that includes one or more cells, etc.) can be introduced on the apical channel 212 side of the overlapping portion 220. In some implementations, a cell culture can be introduced on the basal channel 202 side of the overlapping portion 220. In some implementations, cell cultures can be introduced on both the apical channel 212 side and the basal channel 202 side of the overlapping portion 220. The cell cultures on each side of the scaffold can be the same or different from one another. In some implementations, fluid samples can be introduced into the basal channel 202 via the ports 204 and fluid samples can be introduced into the apical channel 212 via the ports 214. The fluid samples may include, for example, therapeutic substances such as drugs, cells, or any other type of particle or component. Thus, interactions between the cell cultures and the substances included in the fluid samples can be observed in the overlapping portion 220.

In some implementations, two different fluid samples can move through the overlapping portion 220 on both sides of the apical channel 212 and the basal channel 202, causing cells to be trapped on the overlapping region 220 in both the apical channel 212 and the basal channel 202. The two different fluid samples may include two different types of cells, causing one surface of the overlapping portion 202 in one of the basal channel 202 or the apical channel 212 to trap one type of cell, and another surface of the overlapping portion 202 in one of the basal channel 202 or the apical channel 212 to trap one type of cell. Although FIG. 2 is depicted as having two channels, it should be understood that the microfluidic device 102 can include any number of channels and overlapping regions 220. In implementations where the microfluidic device 102 has more than two channels, the overlapping regions 220 of can overlap with one or more of other channels in the microfluidic device 102, and can facilitate fluid flow between any of the channels while trapping cells contained in the fluid flow on one or more surfaces of the overlapping region 220.

The overlapping portion 220 can be treated using one or more treatment processes to improve cell attachment on one or more areas of the overlapping region 220. To culture cells in a particular arrangement for layer analysis, it can be beneficial to cause certain portions of the overlapping region 220 to have properties that encourage cell trapping. In some implementations, it may be desirable for cells not to adhere to a portion of the overlapping region, and thus that portion of the overlapping region can be treated to prevent one or more types of cells from adhering to that portion of the overlapping region 220. Certain cells may have chemicals present on their cellular membrane, cellular wall, or extracellular matrix that bind to certain treated properties of the overlapping region 220. Thus, certain portions of the overlapping region 220 can be treated to target attachment of particular cells or cell types.

The surfaces of the overlapping region 220 can be treated precisely, such that cells adhere to desired portions of the overlapping region 220, while not adhering to undesired portions of the overlapping region 220. To facilitate such functionality, the overlapping region 220 can be treated, for example chemically treated, by at least one of a coating, an energetic plasma treatment, by affixing one or more surfaces of the overlapping region 220 with a self-assembled monolayer, or by surface depositing on one or more portions of the overlapping region 220. In some implementations, portions of the overlapping region 220 can comprise membranes that facilitate cell attachment or trapping (e.g., for particular desired cells or cells generally, etc.), and other portions of the overlapping region can comprise materials that do not facilitate cell attachment or trapping.

Figure 3:
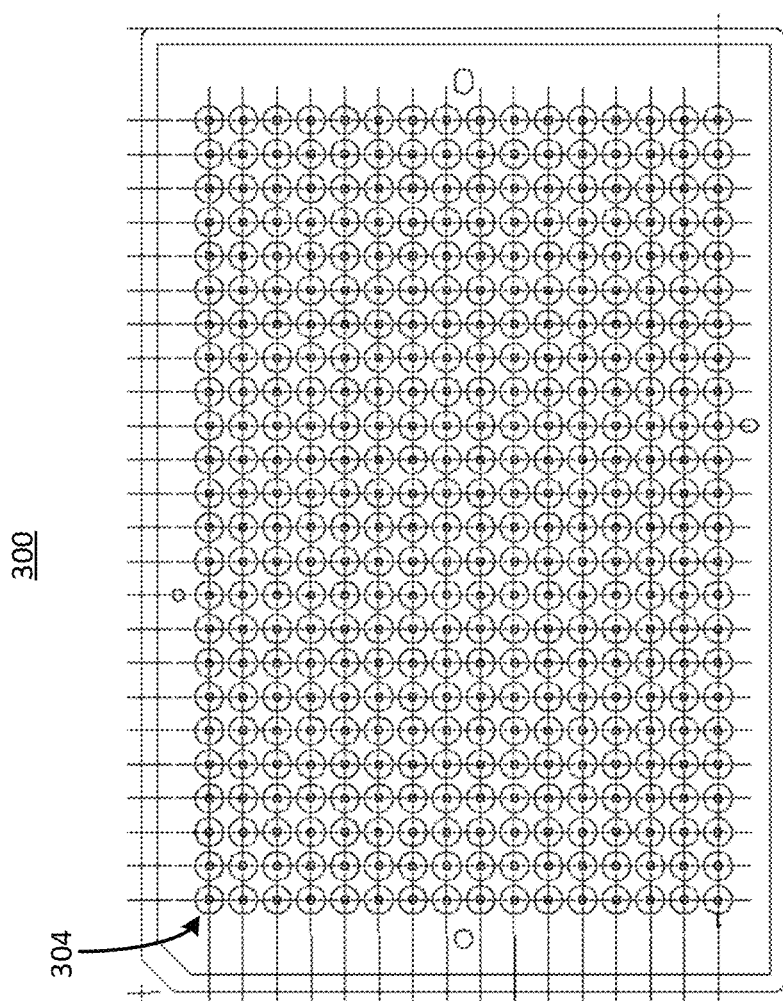
FIG. 3 illustrates a top view of example circular openings in an example well plate, in accordance with an illustrative embodiment.

Referring now to FIG. 3, illustrated is a top view of example circular openings in an example well plate, in accordance with an illustrative embodiment. The well plate 300 can be similar to, or the same as, the well plate 100 described herein above in conjunction with FIG. 1 or the well plate 400 described herein below in conjunction with FIG. 4. The well plate 300 can include one or more ports 304. One or more of the ports 304 can be coupled to, or form one or more portions of, one or more channels of the microfluidic device 102 described herein. In some implementations, the ports 304 can be arranged in a 24 by 16 rectangular array, for a total of 384 ports. Although the ports 304 of the well plate 300 are shown in a rectangular arrangement, it should be understood that any number or arrangement of the ports 304 are possible, and the shape, size, and configuration of any channels coupled to or forming a part of the ports 304 can be altered to conform to the number or arrangement of the ports 304.

In some implementations, one or more ports 304 of the well plate 300 can serve as a port for a basal channel 202 or an apical channel 212, similar to the ports 204 and the ports 214 described herein above in conjunction with FIG. 2. For example, groups of ports 304, such as groups including four ports, can serve as the set of ports for a microfluidic device 102 described herein above in conjunction with FIGS. 1 and 2. In some implementations, a port 304 of the well plate 300 can serve as a port for more than one microfluidic device 102, thereby facilitating fluid flow through multiple microfluidic devices 102 via a single port. In some implementations, the well plate 300 having up to 384 ports can be used to support up to 96 microfluidic devices 102 (e.g., cell culture units). The ports 304 can each have a circular shape as depicted in FIG. 3. The circular shape of the ports 304 of the well plate 300 can be configured to receive a cell seeding tool, such that the circular openings of the ports 304 form a seal with a circular portion of the cell seeding tool. Ports of various well plates, such as the ports 304 of the well plate 300, are described in further detail below in conjunction with FIGS. 5, 6A, and 6B.

Figure 4:
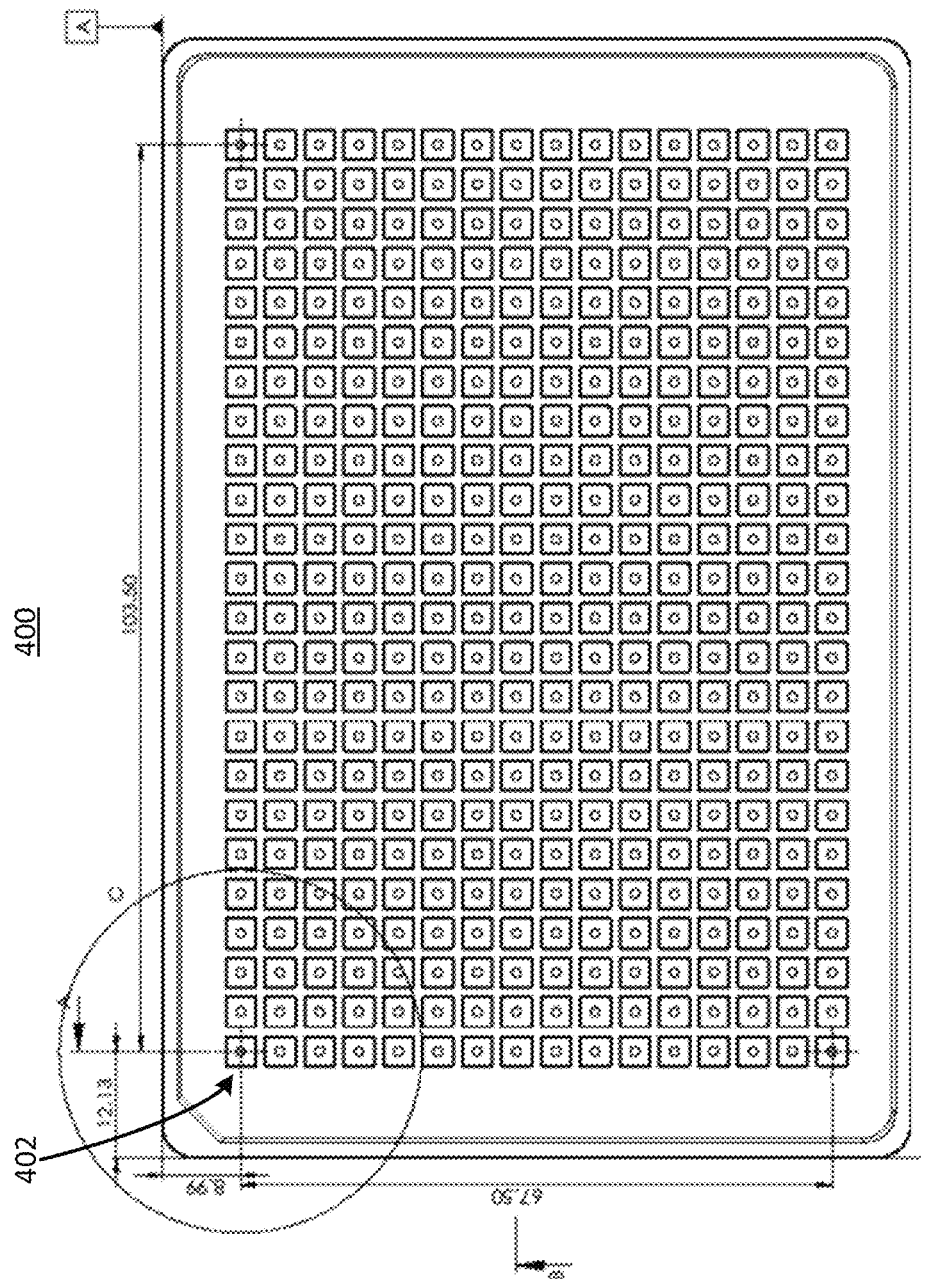
FIG. 4 illustrates a top view of example square openings in an example well plate, in accordance with an illustrative embodiment.

Referring now to FIG. 4, illustrated is a top view of example square openings in an example well plate 400. The well plate 400 can be similar to, or the same as, the well plate 100 described herein above in conjunction with FIG. 1 or the well plate 400 described herein below in conjunction with FIG. 4. The well plate 400 can include one or more ports 404. The ports 404 can be arranged in a 24 by 16 rectangular array, for a total of 384 ports. Although the ports 404 of the well plate 400 are shown in a rectangular arrangement, it should be understood that any number or arrangement of the ports 404 are possible, and the shape, size, and configuration of the channels can be altered to conform to the number or arrangement of the ports 404.

The ports 404 can be similar to the ports 304 described herein above in conjunction with FIG. 3. As depicted in FIG. 4, the ports 404 can have a square cross-sectional shape, rather than a circular shape. In some implementations, the ports 404 of the well plate 400 can be used to form up to 96 microfluidic devices 102, similar to the microfluidic device 102 described herein above in conjunction with FIGS. 1 and 2. In some implementations, a port 404 of the well plate 400 can serve as a port for more than one microfluidic device 102, thereby facilitating fluid flow through multiple microfluidic devices 102 via a single port. In some implementations, the well plate 400 having up to 384 ports can be used to support up to 96 microfluidic devices 102 (e.g., cell culture units). The circular shape of the ports 404 of the well plate 400 can be configured to receive a cell seeding tool, such that the circular openings of the ports 404 form a seal with a circular portion of the cell seeding tool. Ports of various well plates, such as the ports 404 of the well plate 400, are described in further detail below in conjunction with FIGS. 5, 6A, and 6B.

Figure 5:
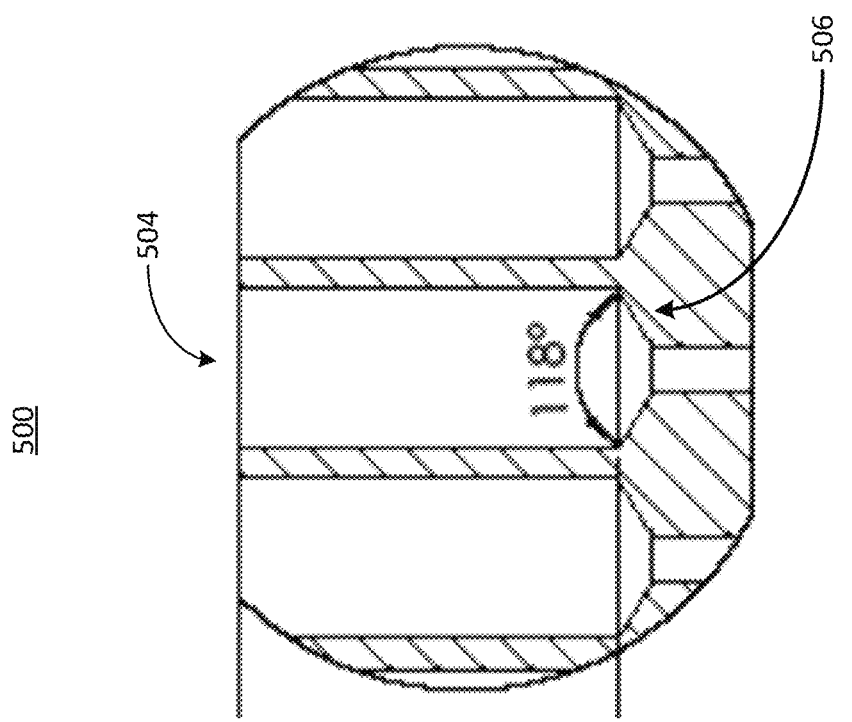
FIG. 5 illustrates a cross-sectional view of an example port of an example well plate, in accordance with an illustrative embodiment.

Referring now to FIG. 5, illustrated is a cross-sectional view of an example port of an example well plate, in accordance with an illustrative embodiment. The well plate 500 can be similar to the well plates 100, 300, and 400 shown in FIGS. 1, 3, and 4, respectively. The well plate 500 can include one or more ports 504. Each port 504 can include a microfluidic feature 506. The microfluidic feature can be any feature that facilitates the delivery of cells from a cell seeding tool to a microfluidic device, such as the microfluidic device 102. In some implementations, one or more of the basal ports 204 or the apical ports 214 can be coupled to or form a part of the well plate 500. In some implementations, the diameter (sometimes referred to as a width) of the opening of the port 504 of the well plate 500 can be greater than the diameter (sometimes referred to as a width) of the opening of the port (e.g., the basal port 204 or the apical port 214, or any other opening, etc.) of the microfluidic device 102. In such implementations, the microfluidic feature 506 can guide a cell seeding tool such that the contents of the cell seeding tool, such as a fluid sample including cells, is delivered to one or more channels (e.g., the apical channel 212, the basal channel 202, any other channel, etc.) of the microfluidic device 102. For example, a tapered microfluidic feature 506 can serve to guide a cell seeding tool from the opening of the well 504 to an opening of a port of the microfluidic device 102. Thus, the microfluidic feature 506 can be coupled to or define the diameter of the port of the microfluidic device 102, and can be configured to guide objects inserted into the well 504 into the port of the microfluidic device 102.

As shown in the example port 504 in FIG. 5, the microfluidic feature 506 can include a rounded tapering of a portion of its respective port 504. The microfluidic feature 506 can be any geometric feature configured to create a seal with a cell seeding tool. In addition to guiding the cell seeding tool to an opening (e.g., a port) of a microfluidic device 102. For example, the seal can be created by a tight fit between the microfluidic feature 506 and the cell seeding tool. The seal can comprise a gasket for other type of sealant. In some implementations, the microfluidic feature 506 can be configured to receive a gasket, such as a gasket that is coupled to or forms a part of the cell seeding tool 504. The tight fit between the cell seeding tool and the port of the microfluidic device 102 can increase the fluid pressure as the fluid sample containing cells is provided by the cell seeding tool. As shown in FIG. 5, the microfluidic feature 506 can include a taper having a taper angle. In this example, the taper angle can be 118 degrees. However, it should be understood that the angle of the taper can vary and be any angle from 0 to 180 d.

Thus, the microfluidic feature 506, such as seal or other configuration as described herein, can help to more efficiently introduce cells into the well plate 500, as compared to standard well plates that may not include the microfluidic features 506 in their respective ports 504, as described further below. It should be understood that the rounded tapering used to implement the microfluidic feature 506 as depicted in FIG. 5 is illustrative only, and in some implementations the microfluidic feature may have a different shape or size. For example, in some implementations, the diameter (sometimes referred to as the width) of the opening of the port 504 of the well plate 500 can be similar to or the same size as the diameter (sometimes referred to as the width) of the port of the microfluidic device 102. In such implementations, a taper may not be needed, and thus the microfluidic feature may have another shape or configuration that can facilitate the delivery of cells by the cell seeding tool to the microfluidic device 102. For example, the microfluidic feature 506 can be a gasket configured to create a seal between an opening of the microfluidic device 102 and a cell seeding tool inserted in or received by the well 504. The microfluidic feature 506 can have be any other type of feature as described herein.

Figure 6A:
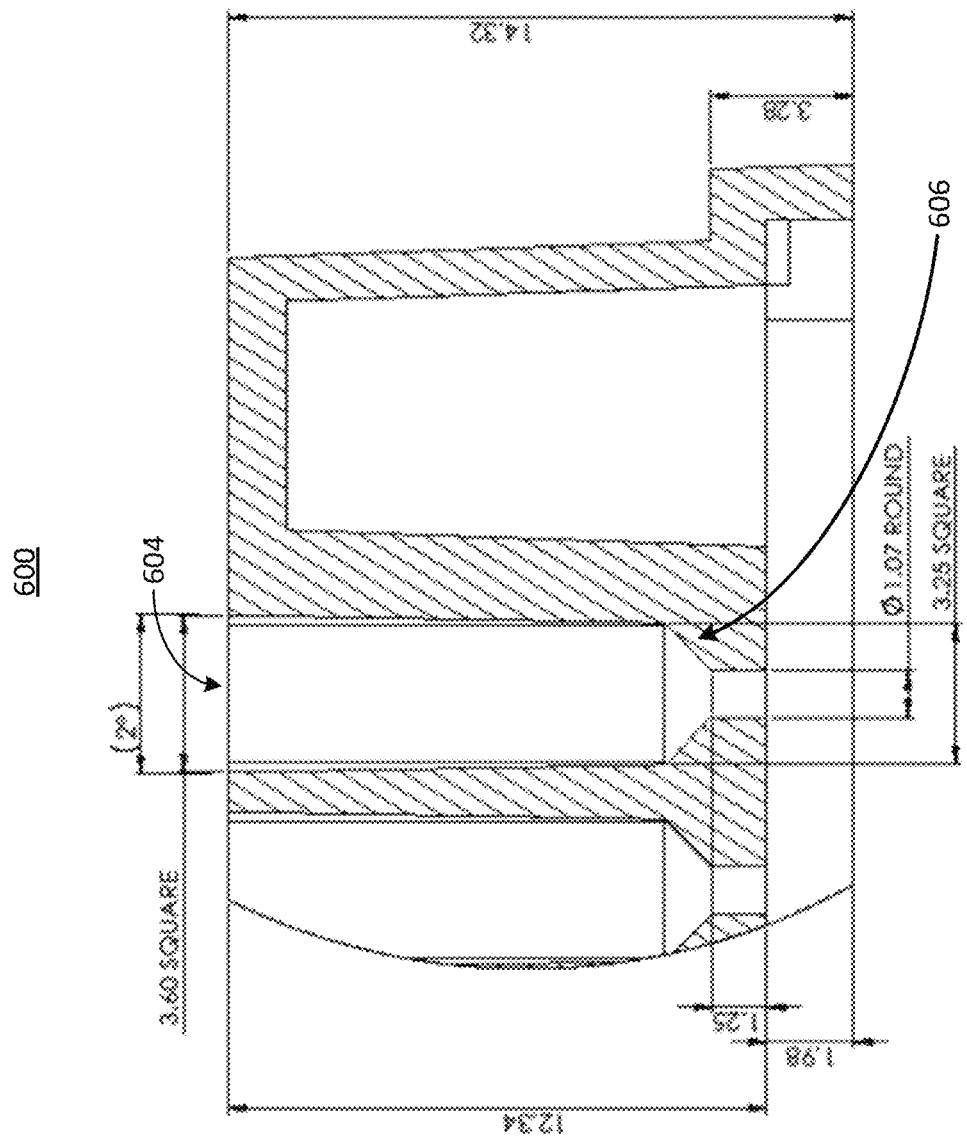
FIG. 6A illustrates a cross-sectional view of another example port of a well plate, in accordance with an illustrative embodiment.

Referring now to FIG. 6A, illustrated is a cross-sectional view of another example port of a well plate 600, in accordance with an illustrative embodiment. The well plate 600 can be similar to the well plates 100, 300, 400, and 500 shown in FIGS. 1, 3, 4, and 5, respectively. The well plate 600 can include one or more ports 604. Each port 604 can include a microfluidic feature 606. In the example of FIG. 6, the microfluidic feature 606 includes a squared tapering of a portion of its respective port 604. However, as described above in conjunction with FIG. 5, the microfluidic feature 606 can be any geometric feature configured to create a seal with a cell seeding tool. Like the other microfluidic features described herein, the microfluidic feature 606 can have various dimensions, such as a width, a height, and other parameters that cause the feature to guide or otherwise receive a cell seeding tool. The microfluidic feature 606 can guide a cell seeding tool inserted into the well 604 to an opening (e.g., a port, etc.) of a microfluidic device 102, which may be coupled to or form a part of the well plate 600. Further, the microfluidic feature 606 can include various mechanical properties, such as fins, gaskets, flanges, or other aspects, that create a seal between a portion of the well 604 and the cell seeding tool.

For example, in some implementations the cell seeding tool can be a pipettor or other liquid handling tool. The shape of the microfluidic feature 606 can create a seal with the cell seeding tool to enable a pressure-driven flow (e.g., pressure created by the cell seeding tool to cause the fluid to flow through the microfluidic device 102, etc.) to push fluid down one or more channels of the microfluidic device 102 and through pores of an overlapping region 220 described herein above in conjunction with FIG. 2, which can include cell scaffold on which the cells are to be seeded. In contrast, traditional gravity fed seeding of cells may not create enough pressure to drive fluid through the pores since the pores have significant resistance to flow due to their diameters, which may range from 0.4 µm to 8 µm, for example. Because the cells cannot pass through the pores, they can be carried by the flow to the membrane where they are stopped by and contact the membrane, or other cell trapping feature of the overlapping region 220 as described herein above in conjunction with FIG. 2.

In some implementations, the microfluidic feature 606, or any other microfluidic feature described herein such as the microfluidic feature 506, can include a simple taper, a taper with multiple steps or ledges, or a taper that varies in angle along the path of fluid flow. The taper can be adjusted to be similar to the taper of the cell seeding tool, such that either the tool and taper make contact or the taper and tool are in very close proximity such that the gap between them restricts fluid flow between them, thereby forcing the fluid flow to pass into the a channel (e.g., a channel of a microfluidic device 102 that forms a part of or is coupled to the well plate 600, etc.) at the end of the port 604. The microfluidic feature 606, or any other microfluidic feature described herein such as the microfluidic feature 506, can be or include a surface roughness, surface topography, or other small scale feature that enables inherent structural flexing to accommodate variations in cell seeding tool diameter and taper. For example, the microfluidic feature 606, or any other microfluidic feature described herein such as the microfluidic feature 506, can be or can include a series of thin flanges that are concentric with the taper that they contact the cell seeding tool. In some implementations, the flanges can be sufficiently thin to allow them to flex mechanically to accommodate various dimensions of the cell seeding tool. The flanges can also be divided around their circumference into small flaps which will allow additional flexing.

In some implementations, the microfluidic feature 606, or any other microfluidic feature described herein such as the microfluidic feature 506, can be or include a chamfer, a flange, a countersink, or an extension into the well or port 604 area of the well plate 600. The microfluidic feature 606, or any other microfluidic feature described herein such as the microfluidic feature 506, can be or include one or more fins or other protrusions, which can run parallel to the axis of the well and seeding tool to align, center, and provide contact with the cell seeding tool spacing it a known distance from the walls of the well or port 604. In some implementations, such fins can be angled, slanted, or curved into a continuous fin, which can be similar to a screw thread. In some implementations, the microfluidic feature 606, or any other microfluidic feature described herein such as the microfluidic feature 506, can be a thread similar to or the same as a screw thread, configured to engage with threads of a microfluidic device. For example, the microfluidic feature 606, or any other microfluidic feature described herein such as the microfluidic feature 506, can include female threads configured to engage with male threads present on a cell seeding tool.

Figure 6B:
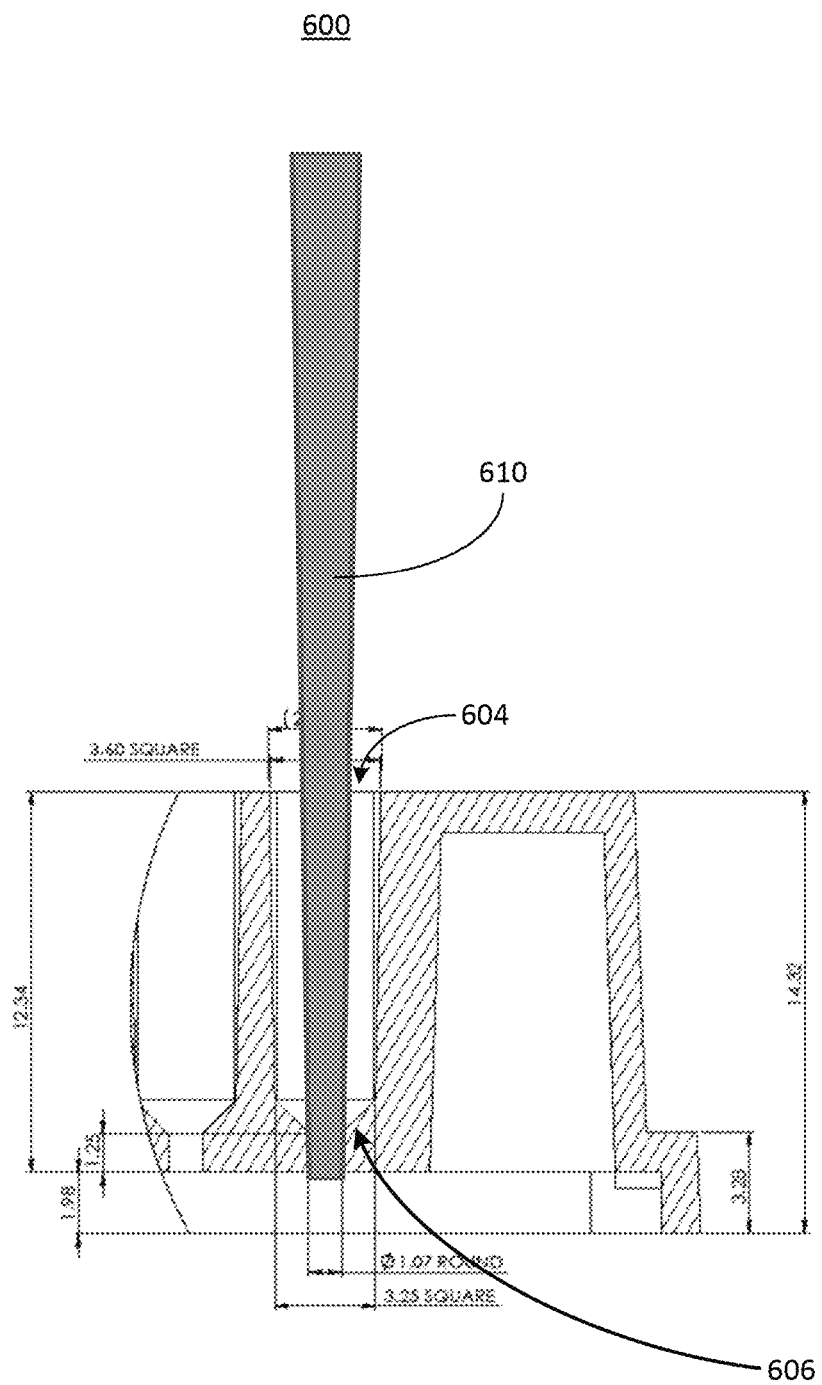
FIG. 6B illustrates a cross-sectional view of an example port receiving a cell seeding tool, in accordance with an illustrative embodiment.

Referring now to FIG. 6B, illustrated is a cross-sectional view of the example port 604 described herein above in conjunction with FIG. 6A with a cell seeding tool 610. The cell seeding tool 610 can be inserted through the port 604. As shown, the cell seeding tool 610 can extend into the port 604 to interface, contact, or otherwise engage with the microfluidic feature 606, such that a seal is created between the microfluidic feature 606 and the cell seeding tool 610. The seal can help to ensure that fluid flow exiting the cell seeding tool 610 is entirely or otherwise substantially directed downward into a channel (e.g., such as a channel of the microfluidic device 102, etc.) beneath the port 604. As shown, the microfluidic feature 606 forms a seal with and guides the cell seeding tool 610 into a port having a second diameter that is smaller than the diameter of the port 604 of the well plate 600. However, it should be understood that the width of the second port (e.g., the opening of the microfluidic device 102, etc.) need not be smaller than the opening of the port or well 604 of the well plate 600, and can instead be any size. As a result, cells can be introduced through the port 604 via the cell seeding tool 610 with a higher pressure (and therefore a higher precision) than gravity-based cell seeding can provide. The higher pressure can cause the fluid sample including the cells to be forced through the overlapping portion 220 described herein above in conjunction with FIG. 2. The cell seeding tool 610 can be a pipette tip, a pipettor, a sero-pipette, a syringe tip, or another small volume fluid handling tool.

In some implementations, the cell seeding tool 610 can be a device to deliver pressure to all ports simultaneously after they have been filled with solutions of cells. For example, each of the wells 604 of the well plate 600 can be filled by a device with a fluid sample containing one or more cells. In some implementations, the device that fills each of the wells 604 with the fluid sample can be the cell seeding tool 610. Next, a cell seeding tool can be inserted into and form a seal with the well 604 of the well plate 600. The cell seeding tool 610 can then create a positive pressure in the well 604, thereby forcing the fluid sample deposited into the well 604 through one or more channels (e.g., of a microfluidic device 102, etc.) coupled to or forming a part of the well plate 600.

In some implementations, a spacer or gasket can also be included on top of the well plate 600, or as a part of the microfluidic feature 606. The spacer or gasket can help to align or space the cell seeding tool 610 a known distance from the seeding port 604 or cell culture surface. In some implementations, such a spacer can be partially inserted into or be a part of the port 604. The spacer or gasket can allow pressure to be generated within the well by the cell seeding tool 610 without necessitating contact of the cell seeding tool 610 with the inner walls of the well or the port 604. In some implementations, the microfluidic feature 606 can include the gasket or spacer to create a seal between the cell seeding tool and an opening of a channel of a microfluidic device 102, which can be a part of or can be coupled to the wells of the well plate 600.

Referring now to FIG. 7, depicted is a cross-sectional view of an example cell scaffold, in accordance with an illustrative embodiment. The scaffold 702 can be seeded with cell cultures using a cell seeding tool similar to the cell seeding tool 610 described herein above in conjunction with FIG. 6B. The scaffold can be, or may form a part of, the overlapping region 220 described herein above in conjunction with FIG. 2. Thus, different cell cultures can be seeded on one or more surfaces of the cell scaffold, each surface being disposed within a channel of a microfluidic device 102 as described herein above in conjunction with FIGS. 1 and 2. For example, a first cell culture 704 can be seeded on a first side of the scaffold 702. The first side (sometimes referred to as a first surface) of the scaffold can be disposed within a channel of the microfluidic device 102, such as the apical channel 212, the basal channel 202, or any other channel of the microfluidic device 102. A fluid sample containing a first type of cell can be introduced to and forced through the channel. The cell scaffolding can be configured to trap or attached the cells on the scaffold or other type of membrane while allowing the other components of the fluid sample to pass through the cell scaffold and into another channel of the microfluidic device 102.

Likewise, the cell scaffold can perform the same functions for a second fluid sample including a second cell culture 706 introduced on a second side or surface of the scaffold 702. For example, the second fluid sample can be introduced in a channel different than the channel used to introduce the first fluid sample to the cell scaffold. The cell culture 704 can include cells that are of the same type or of a different type from the cells included in the cell culture 706. The second side (sometimes referred to as a second surface) of the scaffold can be disposed within a second channel of the microfluidic device 102, such as the apical channel 212, the basal channel 202, or any other channel of the microfluidic device 102. A second fluid sample containing a second type of cell can be introduced to and forced through the channel. The cell scaffolding can be configured to trap or attached the cells on the scaffold while allowing the other components of the fluid sample to pass through the cell scaffold or other type of membrane and into another channel of the microfluidic device 102.

In some implementations, the cell cultures 704 and 706 can adhere to the scaffold 702 (e.g., or any other part of the overlapping portion 220, etc.) through adhesion mechanisms, at least some of which may be inherent to adhesive cells. In some implementations, the flow of fluid exiting the cell seeding tool can follow a path leading through the scaffold 702 created by a pressure gradient, or other type of pathway of the microfluidic device 102. Therefore, cells can be predominantly deposited on the scaffold, rather than in surrounding areas. This can improve control over cell seeding locations, relative to gravity fed cell seeding or other cell seeding techniques. Additionally, because the flow of fluid out of the cell seeding tool can be the driving force to direct deposition of cells, the cells also be deposited on the bottom of the scaffold 702 by forcing flow through the scaffold from bottom to top (e.g., from the basal channel 202 to the apical channel 212, etc.), which may not be possible with gravity fed cell seeding. Thus, cell seeding can be achieved on two opposite sides of a scaffold, as depicted in FIG. 7.

In some implementations, the scaffold 702 (e.g., or any part of the overlapping portion 220, etc.) can be or can include any of a membrane, a filter, a mesh, or other substance that allows liquid to be forced through it while trapping cells on it so they can adhere, spread and grow. Thus, the scaffold 702 can be, be a part of, or include any of the aspects of the overlapping portion 220 described herein above in conjunction with FIG. 2. Pore sizes, mesh spacing, or general transport properties of the scaffold 702 can be adjusted to control the relation between cell attachment, fluid flow, and pressure driving the fluid flow. In some implementations, the scaffold 702 can be designed for a desired hydraulic resistance along with cell attachment properties. In some implementations, the scaffold 702 can also be a porous mesh, gel, or other material that allows preferential transport of liquid through it while limiting cell transport through it.

The scaffold 702 can be embossed, etched, laser machined, mechanically machined, ablated or otherwise patterned with mechanical surface features to influence cell attachment, adhesion, spreading, or other cell properties. The scaffold 702 can also be coated, energetically treated via a plasma or other means, affixed with a self-assembled monolayer, surface deposited, or otherwise modified chemically to have chemical surface features to influence cell attachment, adhesion, spreading, or other cell properties. In some implementations, the scaffold 702 can have both mechanical and chemical surface features, with either or both such features placed on the scaffold in selected areas so that cell properties are modified within those areas. For example, some areas of the scaffold 702 can have a chemical surface modification to limit cell attachment while others would have a mechanical surface modification to encourage cell attachment. Certain portions of the scaffold 702 can be treated to improve cell attachment, while other portions may not be treated to encourage cell attachment, thereby allowing precise cell seeding on the scaffold 702 of the microfluidic device 102.

Thus, a cell seeding technique according to this disclosure can include introducing cells or clusters of cells into a liquid solution, drawing the liquid solution into a pipettor or other cell seeding tool, and pushing the solution of cells out through the seeding tool and through a port into a microfluidic channel of a well plate. The tip of the cell seeding tool can be pressed against a microfluidic feature, such as the microfluidic features 506 and 606 shown in FIGS. 5, 6A, and 6B, with enough force that a seal is formed. In some implementations, the wells 504 and the wells 604 of the wells 500 and 600 respectively can be filled with one or more liquid solutions, and the cell seeding tool can create a pressure within the well 504 and 604 to force the liquid solution through a microfluidic device 102 that is coupled to or formed as a part of the well plate 500 or 600, respectively. A seal can be created between the cell seeding tool and one or more portions of the well plate 500 or 600 or the microfluidic device 102, such that the pressure created by the cell seeding tool does not escape the well plate 500 or 600 and instead forces the liquid solution through one or more microfluidic devices 102.

The seal can prevent flow from escaping up into a well or reservoir, thus forcing the flow to enter one or more channels of one or more microfluidic devices 102. In some implementations, a cell seeding tool can be inserted into each port of a microchannel (e.g., ports at opposite ends of a microchannel, such as the ports 204a and 204b of the basal channel 202 or the ports 214a and 214b of the apical channel as described above in conjunction with FIG. 2, etc.). For example, if each microfluidic channel has an inlet and outlet port, a cell seeding tool can be inserted into both the inlet port and the outlet ports simultaneously. Both cell seeding tools can be actuated simultaneously to force the solution of cells into both inlet and outlet. The path for the fluid to escape can therefore be through the pores of the overlapping region 220 in the channel of the microfluidic device 102, resulting in flow going through the scaffold and depositing cells to the scaffold surface. In this way the flow can preferentially deposit cells where there is flow through the membrane (e.g., the overlapping region 220, etc.). In an overlapping microchannel device, the flow through the membrane may be only in the overlapping area, which is can be a desirable area for cell attachment and analysis.

In some implementations, a cell seeding tool can be inserted into one port of a microfluidic channel, and the remaining ports can be plugged, for example with a stopper or other object to prevent pressure or fluid from escaping the plugged wells. In this example, the cell seeding tool can provide a fluid sample including a cell solution, while the plugs prevent flow out of any other ports, resulting in flow through the scaffold pores (e.g., the overlapping region 220, etc.). Thus, plugs can be used to guide the flow of a fluid sample through a microfluidic device 102. In some implementations, solutions of cells can be placed into all ports, and then pressure can be applied to all ports, for example by using a gasket and delivery of pressurized gas or other fluid to the ports. The cell seeding tool can be configured to provide the pressure via the pressurized gas or other fluid to the ports via one or more pumps, for example. The pressurized gas or fluid can force fluid into the microfluidic channels, and the gasket can seal against any flow going back into the ports. As a result, flow can pass through the scaffold pores (e.g., the overlapping region 220, etc.) and cells can attach to the scaffold as desired.

Thus, the overlapping region 220, which can be or include the scaffold 702, can provide precise seeding and culturing of cells in any desired location or surface of the overlapping region 220 of the microfluidic device 102. Culturing the cells in desired locations can result in a model of a tissue of interest, such as a portion of an organ, a portion of an organism such as bacteria, or any other arrangement of any other type of biological cell. The resulting tissue model, generated by using the techniques of this disclosure, can include cells precisely positioned in selected areas of a scaffold (e.g., selected by particular treatments to the overlapping region 220, and particular delivery to certain surfaces of the overlapping region 220, etc.). Cells can thus be seeded to or cultured on one or more sides or surfaces of the scaffold (e.g., one or more portions of the overlapping region 220).

Multiple types of cells can be seeded to one or more sides or surfaces of the scaffold (e.g., the overlapping region 220). In some implementations, multiple cell types can be seeded simultaneously using a mixture of cells in the solution of cells. In some implementations, each cell type can be seeded separately. In some implementations, cells can be seeded while in a gel. In some implementations, pluripotent, totipotent, or otherwise undifferentiated cells can be seeded into the device and allowed to remain in their initial state or triggered to differentiate. In some implementations, fully or partially differentiated cells can be seeded into the device. In some implementations, clusters of cells, cell spheroids, cell organoids, or fragments of tissue can be seeded into the device. In some implementations typically "unplateable" cells, i.e. those that do not readily adhere to a surface, can be plated to a surface using this technique rendering them "plateable." As described herein, the term "seeding" can refer to the act of attaching cells from a particular medium (e.g., fluid sample, gel, any other media described herein, etc.) to an overlapping portion of the microfluidic device 102.

Figure 8:
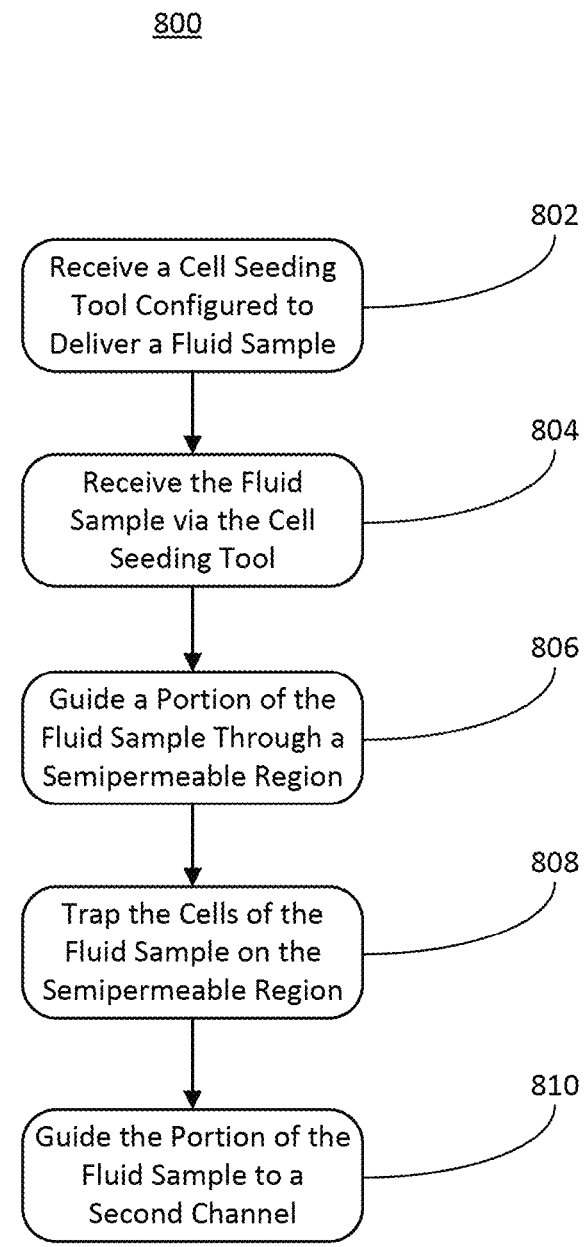
FIG. 8 depicts a flow diagram of an example method of seeding cell cultures using a microfluidic device, in accordance with an illustrative embodiment.

Referring now FIG. 8, depicted is a flow diagram of an example method 800 of seeding cell cultures using a microfluidic device, in accordance with an illustrative embodiment. In brief overview of the method 800, a first channel (e.g., one of the basal channel 202 or the apical channel 212 of the microfluidic device 102, any other channel of the microfluidic device 102 as described herein, etc.) of a microfluidic device (e.g., the microfluidic device 102, etc.) can receive a cell seeding tool (e.g., the cell seeding tool 610, etc.) configured to deliver a fluid sample comprising cells (STEP 802), the first channel of the microfluidic device can receive the fluid sample via the cell seeding tool (STEP 804), the microfluidic device can guide a portion of the fluid sample through a semipermeable membrane of the microfluidic device (STEP 806), the microfluidic device can trap the cells of the fluid sample within the first channel (STEP 808), and the microfluidic device can guide the portion of the fluid sample to a second channel coupled to the semipermeable membrane (STEP 810).

In further detail of the method 800, a first channel (e.g., one of the basal channel 202 or the apical channel 212 of the microfluidic device 102, any other channel of the microfluidic device 102 as described herein, etc.) of a microfluidic device (e.g., the microfluidic device 102, etc.) can receive a cell seeding tool (e.g., the cell seeding tool 610, etc.) configured to deliver a fluid sample comprising cells (STEP 802). The cell seeding tool can be inserted through a port or opening of a well plate, or inserted into a port or opening of a channel of the microfluidic device. The opening in the well plate can be coupled to or be a part of the opening of a channel of the microfluidic device. In some implementations, the cell seeding tool can interface, contact, or otherwise engage with a microfluidic feature in a port of the microfluidic device (e.g., the ports 204 of the basal channel 202 or the ports 214 of the apical channel 214, etc.), such that a seal is created between the port (e.g., via a microfluidic feature as described herein) and the cell seeding tool. The seal can ensure that a fluid flow exiting the cell seeding tool is entirely or otherwise substantially directed downward into a channel (e.g., such as a channel of the microfluidic device 102, etc.) of the microfluidic device. The cell seeding tool can be a pipette tip, a pipettor, a sero-pipette, a syringe tip, or another small volume fluid handling tool. In some implementations, a second port of the microfluidic device (e.g., of the first or a second channel of the microfluidic device) can receive a second cell seeding tool in a similar manner, such that a seal is also created between the second port and the second cell seeding tool.

The first channel of the microfluidic device can receive the fluid sample via the cell seeding tool (STEP 804). The cell seeding tool received by the first channel of the microfluidic device can provide a fluid pressure inside the channel (e.g., the apical channel 212 or the basal channel 202, any other channel described herein, etc.), where the cell seeding tool has been received. The fluid pressure can force the fluid sample from the cell seeding tool and into the microfluidic channel of the microfluidic device. Because the cell seeding tool can create a seal with a port of the microfluidic device, the fluid pressure can be maintained by the cell seeding tool within the microfluidic device. Cells can be introduced through a port of a well plate or a port of the microfluidic device via the cell seeding tool as part of the fluid sample with a higher pressure (and therefore a higher precision) than gravity-based cell seeding can provide. The higher pressure can further cause the fluid sample including the cells to be forced through an overlapping portion of the microfluidic device (e.g., the overlapping portion 220 described herein above in conjunction with FIG. 2, etc.).

The microfluidic device can guide a portion of the fluid sample through a semipermeable membrane of the microfluidic device (STEP 806). The high pressure created by the cell seeding tool and maintained by the seal between the cell seeding tool and the well plate or the one or more ports of the microfluidic device can cause the fluid sample provided by the cell seeding tool to flow through one or more channels of microfluidic device. The channels in the microfluidic device can have an overlapping portion (e.g., the overlapping portion 220 described herein above in conjunction with FIG. 2, etc.). The channels of the microfluidic device can be configured to cause fluid forced through the channel to follow a pathway through a semipermeable portion of the overlapping region. For example, the overlapping portion can form a part of the channel through which the fluid sample is forced via the fluid pressure generated by the cell seeding tool. A second channel, (e.g., the other of the basal channel 202 or the apical channel 212 of the microfluidic device 102, etc.) can have a lower pressure than the fluid pressure created in the first channel. Thus, a pressure gradient can form the lowest resistance path such that the fluid flow is guided through the overlapping portion and into the second channel of the microfluidic device. If a second cell seeding tool has been received by the second channel, the second channel can receive a second fluid sample containing second cells, and guide the second fluid sample through the overlapping region, in the same manner as described above.

The microfluidic device can trap the cells of the fluid sample within the first channel (STEP 808). The overlapping region can be configured to trap and grow cell cultures, for example cell cultures or cells within a fluid sample received from a cell seeding tool. The overlapping portion can be porous, or otherwise semipermeable, thus facilitating flow of one or components of a fluid sample between two or more channels between which the overlapping portion is disposed or coupled. The overlapping portion can be made of materials other than the materials that define the channels of the microfluidic device. For example, the overlapping portion can be or include any of a membrane (e.g., a semipermeable membrane, etc.), a filter, a mesh, or any other substance that allows some or all of a fluid to pass through the overlapping portion. Thus, the overlapping portion 220 can facilitate the flow of a fluid sample between the channels of the microfluidic device while trapping cells in the fluid sample on the respective portion of the membrane within the microfluidic device. For example, if a fluid sample containing cells passes through the barrier from a first channel of the microfluidic device into a second channel of the microfluidic device, the overlapping portion can trap the cells of the fluid sample on the surface of the overlapping portion within the first channel. Likewise, if a fluid sample containing cells passes through the overlapping portion from the second channel into the first channel, the overlapping portion can trap the cells of the fluid sample on the surface of the overlapping portion within the second channel of the microfluidic device. The overlapping portion can include a cell scaffold such as a permeable membrane. The scaffold can, at least in part, separate the channels of the microfluidic device while forming a portion of each separated channel. The cell cultures on each side of the overlapping portion can be the same or different from one another.

The microfluidic device can guide the portion of the fluid sample to a second channel coupled to the semipermeable membrane (STEP 810). To facilitate cell trapping, the microfluidic device can transport the other components of the fluid sample (e.g., components not including cells, or components including cells that can pass through the overlapping portion, etc.) from the first channel to the second channel through the overlapping portion. This causes the overlapping portion to act as a cell "filter" by trapping the cells on a wall or surface of a first channel while allowing the rest of the fluid to pass through the overlapping portion without incident. The microfluidic device can perform this in both directions. For example, the second fluid sample delivered by the second cell seeding can pass from the second channel to the first channel through the overlapping portion. In such implementations, the cells in the second fluid sample can be trapped on a surface opposite the surface that has trapped the cells of the first fluid sample. Thus, the microfluidic device can cause fluid samples to pass throughout the channels via the overlapping portion, trapping cells in the process as described herein.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The devices, systems, and methods described herein may be embodied in other specific forms without departing from the characteristics thereof. The foregoing implementations are illustrative rather than limiting of the described devices, systems, and methods. Scope of the devices, systems, and methods described herein is thus indicated by the appended claims, rather than the foregoing description, and changes that come within the meaning and range of equivalency of the claims are embraced therein.

What is claimed is:

1. A microfluidic device, comprising:
   a first channel having a first inlet port and a first outlet port, the first channel configured to receive a fluid sample comprising cells, the first inlet port defining a tapered portion that creates a seal between the first inlet port and a cell seeding tool that provides the fluid sample;
   a second channel coupled to the first channel via an overlapping region, the second channel having a second inlet port and a second outlet port; and
   an overlapping region between the first channel and the second channel, configured to trap the cells in the fluid sample as the fluid sample is forced by the cell seeding tool through the overlapping region via the first channel.

2. The microfluidic device of claim 1, wherein the overlapping region forms a bottom portion of the first channel and forms a top portion of the second channel.

3. The microfluidic device of claim 1, wherein at least one of the first inlet port, the first outlet port, the second inlet port, or the second outlet port is coupled to a well of a well plate.

4. The microfluidic device of claim 1, wherein the overlapping region comprises a semipermeable membrane configured to allow the fluid sample to flow from the first channel to the second channel while trapping the cells in the fluid sample on a surface of the semipermeable membrane in the first channel.

5. The microfluidic device of claim 4, wherein the overlapping region is further configured to trap cells in a second fluid sample on a second surface of the semipermeable membrane in the second channel while allowing a second fluid sample to flow from the second channel to the first channel.

6. The microfluidic device of claim 1, wherein the overlapping region comprises at least one of a membrane, a filter, a mesh, or a scaffold.

7. The microfluidic device of claim 1, wherein one or more portions of the overlapping region are chemically treated by at least one of:
   a coating;
   an energetic plasma treatment;
   affixing the one or more portions with a self-assembled monolayer; or
   surface depositing.

8. The microfluidic device of claim 1, wherein an opening of at least one of the second inlet port, the first outlet port, or the second outlet port is defined by a first width and comprises a second tapered portion defining a second width, and is configured to receive a portion of the cell seeding tool.

9. The microfluidic device of claim 8, wherein the tapered portion is at least one of a squared tapering or a rounded tapering.

10. The microfluidic device of claim 8, wherein the tapered portion comprises one or more flanges arranged concentrically with the tapered portion that mechanically flex to accommodate the cell seeding tool.

11. The microfluidic device of claim 8, wherein the opening of at least one of the the second inlet port, the first outlet port, or the second outlet port comprises at least one of a gasket or a spacer configured to create a seal with the portion of the cell seeding tool.

12. The microfluidic device of claim 1, wherein an opening of at least one of the first inlet port, the second inlet port, the first outlet port, or the second outlet port comprises at least one of one or more fins, a chamfer, a countersink, or an extension into a well of a well plate.

13. A system, comprising:
- a semipermeable membrane having a first surface and a second surface opposite the first surface, each of the first surface and the second surface configured to trap cells in a fluid sample;
- a first channel coupled to the semipermeable membrane and having a first portion defined by the first surface of the semipermeable membrane, the first channel comprising an inlet port defining a tapered portion that creates a seal between the inlet port and a cell seeding tool that provides the fluid sample; and
- a second channel coupled to the semipermeable membrane and having a second portion defined by the second surface of the semipermeable membrane,
- wherein the semipermeable membrane is configured to allow the fluid sample to flow between the first channel and the second channel as the fluid sample is forced by the cell seeding tool through the semipermeable membrane.

14. The system of claim 13, wherein the semipermeable membrane comprises at least one of a membrane, a filter, a mesh, or a scaffold.

15. The system of claim 13, wherein the semipermeable membrane is further configured to:
- trap, on the first surface, first cells of a first fluid sample flowing from the first channel to the second channel; and
- trap, on the second surface, second sells of a second fluid sample flowing from the second channel to the first channel.

16. The system of claim 13, wherein a portion of the semipermeable membrane is configured to limit cell attachment.

17. The system of claim 13, wherein at least a portion of the semipermeable membrane is chemically treated by at least one of:
- a coating;
- energetic plasma treatment;
- affixing the one or more surfaces with a self-assembled monolayer; or
- surface depositing.

* * * * *